March 28, 1972 C. F. ZAIGER Plant Pat. 3,087
NECTARINE TREE
Filed July 24, 1969
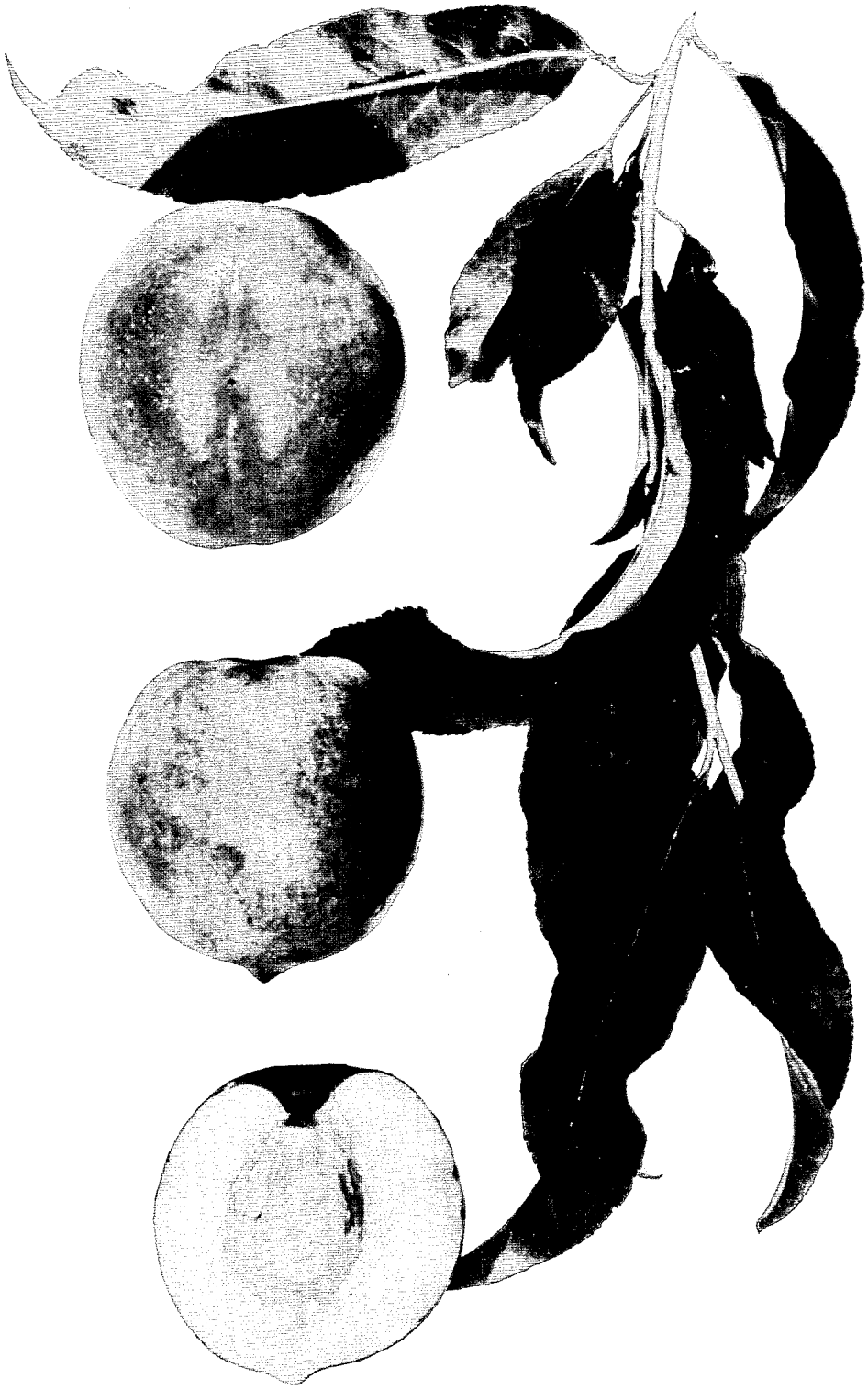
INVENTOR
C. Floyd Zaiger

United States Patent Office

Plant Pat. 3,087
Patented Mar. 28, 1972

3,087
NECTARINE TREE

Chris Floyd Zaiger, 537 Rosemore Ave., Modesto, Calif. 95351

Filed July 24, 1969, Ser. No. 844,672
Int. Cl. A01h *5/03*
U.S. Cl. Plt.—41 1 Claim

My invention relates to a new and distinct variety of nectarine tree which bears yellow-fleshed fruit characterized as to novelty by ripening earlier; the ripening period being approximately 10 days earlier than Grand River (U.S. Plant Pat. No. 1,248). The new variety is also characterized, as to novelty, as having increased productivity and the ability to size a greater number of fruits per tree than other early fruiting nectarine varieties. The fruit colors two to three weeks before ripening; has a greater number of larger, smoother fruit than other early varieties.

The new variety of nectarine tree was originated by me in my experimental orchard near Modesto, Calif., as a second generation seedling from a cross between Early Sun Grand nectarine (U.S. Plant Pat. No. 1,420) and the July Elberta peach (U.S. Plant Pat. No. 30). The present variety was asexually propagated by grafting and budding, as performed at Modesto, Calif., and shows that said characteristics come true to form and are established and transmitted through succeeding propagations.

The following is a detailed description of the foliage and fruit of my new variety, as based upon observations of specimens grown near Modesto, Calif., with color terminology in accordance with Reinhold Color Atlas by A. Kornerup and J. H. Wanscher.

Date of first and last picking: Generally ripens in late May, although over prolonged observation dates of first picking varied from May 28 to June 6 with last picking from June 8 to June 18.

Tree:
- *Size.*—Medium to large.
- *Vigor.*—Medium.
- *Form.*—Spreading.
- *Production.*—Very productive.
- *Bearing.*—Regular bearer.

Trunk:
- *Size.*—Medium to stocky.
- *Surface.*—Medium to shaggy.

Branches:
- *Size.*—Medium to stocky.
- *Surface.*—Medium shaggy.
- *Color.*—Brown to grayish brown.
- *Lenticels.*—Medium quantity.

Leaves:
- *Size.*—Large to medium. Average length 6½". Average width 1⅜".
- *Texture.*—Smooth.
- *Margin.*—Crenate.
- *Petiole.*—Medium length.
- *Glands.*—Primarily reniform.
- *Color.*—Upper surface medium green (27D8). Lower surface lighter green (28D7). Heavy midrib on lower surface yellow green (30B7).

Flower buds:
- *Size.*—Medium.
- *Length.*—Medium.

Flowers:
- *Blooming period.*—Mar. 4 to Mar. 12.
- *Size.*—Large.
- *Color.*—Pink.
- *Pollen.*—Present.

Fruit:
- *Maturity.*—June 8, 1968.
- *Date of first picking.*—June 1, 1968.
- *Date of last picking.*—June 8, 1968.
- *Size.*—Uniform, large to medium. Average diameter axially 2⅜". Average transversely in suture plane 2⅜".
- *Form.*—Uniform, nearly globose.
- *Suture.*—Shallow, extends from base to apex.
- *Ventral surface.*—Rounded slightly.
- *Cavity.*—Elongated in suture plane, with suture showing on both sides.
- *Apex.*—Short.

Skin:
- *Thickness.*—Medium.
- *Texture.*—Tough to medium, tenacious to flesh, slightly rough.
- *Tendency to crack.*—None.
- *Down.*—Wanting.
- *Color.*—Yellow ground color (3A7 to 4A7) almost entirely overspread with red (10B8 to 11C8).

Flesh:
- *Juice.*—Moderate.
- *Texture.*—Firm, crisp, meaty.
- *Ripens.*—Fairly evenly.
- *Flavor.*—Sub-acid.
- *Aroma.*—Very little.
- *Tendency to split.*—Slight.
- *Eating quality.*—Good.
- *Color.*—Yellow orange (5B6 to 5B8).

Stone:
- *Type.*—Cling.
- *Size.*—Medium; average length 1½"; average breadth 1"; average thickness ⅝".
- *Form.*—Ovoid.
- *Base*—Straight.
- *Apex.*—Acuminate.
- *Sides.*—Mostly equal.
- *Surface.*—Pitted throughout.
- *Ridges.*—Rounded.
- *Dorsal edge.*—Narrow.
- *Ventral edge.*—Thin.
- *Tendency to split.*—Slight.
- *Color.*—Light brown (8C5).

Use: Market dessert.

Shipping and keeping quality: Good.

The tree and its fruit herein described may vary in slight detail due to climate and soil conditions under which the variety may be grown. The description is that of the variety produced uder ecological conditions prevailing at Modesto, Calif., and the characteristics are found to hold true in asexual reproduction.

The following is claimed:

1. A new and distinct variety of nectarine tree as illustrated and described which bears large to medium, cling stone fruit having yellow flesh; characterized by ripening approximately 10 days earlier than the Grand River nectarine (Plant Pat. No. 1,248) and the Merrill Sunrise nectarine (Plant Pat. No. 1,256); and further characterized, in comparison with said other varieties, by heavier production of larger size fruits of red color shading to maroon which overspreads a yellow ground color.

No references cited.

ROBERT E. BAGWILL, Primary Examiner